United States Patent [19]
Filmus et al.

[11] Patent Number: 5,877,018
[45] Date of Patent: *Mar. 2, 1999

[54] SYNTHETIC EUKARYOTIC PROMOTERS CONTAINING TWO INDUCIBLE ELEMENTS

[75] Inventors: Jorge Filmus, Toronto; Michel Klein, Willowdale, both of Canada

[73] Assignee: Connaught Laboratories Limited, North York, Canada

[*] Notice: The term of this patent shall not extend beyond the expiration date of Pat. No. 5,559,027.

[21] Appl. No.: 633,289

[22] Filed: Apr. 16, 1996

Related U.S. Application Data

[63] Continuation of Ser. No. 256,720, Oct. 20, 1994, Pat. No. 5,559,027.
[51] Int. Cl.⁶ .......................... C12N 15/85; C12N 15/63; C07H 71/04; C12Q 1/68
[52] U.S. Cl. .......................... 435/325; 435/6; 435/172.3; 435/320.1; 536/23.1; 536/24.1
[58] Field of Search .............................. 435/172.3, 240.2, 435/320.1, 6, 325; 536/23.1, 24.1

[56] References Cited

FOREIGN PATENT DOCUMENTS

WO83/01783  5/1983  WIPO .
WO91/10453  7/1991  WIPO .
WO91/12258  8/1991  WIPO .

OTHER PUBLICATIONS

Filmus, J. et al. "Synergistic induction of promoters containing metal–and glucocorticoid–responsive elements" Nucleic Acids Research. vol. 20, No. 11, Jun. 11, 1992, pp. 2755–2760.

Thompson, et al. "Trans–activation by thyroid hormone receptors: functional parallels with steroid hormone receptors" –Proceedings of the National Academy of Sciences of USA, vol. 86, No. 10, May, 1989, pp. 3494–3498.

Hu et al; Molecular and Cellular Biology, vol. 10, No. 12; pp. 6141–6151, Dec., 1990.

Wright et al; Proceedings of the National Academy of Sciences USA, vol. 88, pp. 8283–8287; Oct., 1991.

Allan et al; The Journal of Biologi cal Chemistry, vol. 266, No. 9; pp. 5905–5910; Mar. 25, 1991.

*Primary Examiner*—George C. Elliott
*Assistant Examiner*—Andrew Wang
*Attorney, Agent, or Firm*—Sim & McBurney

[57] ABSTRACT

Synthetic inducible eukaryotic promoters for the regulation of transcription of a gene achieve improved levels of protein expression and lower basal levels of gene expression. Such promoters contain at least two different classes of inducible elements, usually by modification of a native promoter containing one of the inducible elements by inserting the other of the inducible elements. In embodiments, additional metal responsive elements IR:Es) and/or glucocorticoid responsive elements (GREs) are provided to native promoters, particularly the hMT-IIA and MMTV-LTR promoters. One or more constitutive elements may be functionally disabled to provide the lower basal levels of gene expression.

28 Claims, 1 Drawing Sheet

SYNTHETIC EUKARYOTIC PROMOTERS CONTAINING TWO INDUCIBLE ELEMENTS

This application is a continuation of Ser. No. 08/256,720, filed Oct. 20, 1994, now U.S. Pat. No. 5,559,027.

FIELD OF INVENTION

The present invention relates to the generation of improved inducible mammalian expression systems.

BACKGROUND TO THE INVENTION

Mammalian expression systems are being widely used in the production, by recombinant techniques, of proteins that are extensively modified after translation. These systems can be either constitutive or inducible. It is advisable to use inducible systems for the expression of potentially cytotoxic proteins.

A key element in determining whether an expression system is constitutive or inducible is the promoter. Several mammalian promoters that can be induced in experimental systems have been characterized and promoters present in the metallothionein (MT) genes and in the mouse mammary tumour virus/long terminal repeat (MMTV-LTR) have been used extensively.

The best inducers for the MT promoter are heavy metal ions, such as cadmium (Cd) and zinc (Zn). The induction of the promoter is mediated by transcription factors which, after activation by metals, bind to the inducible metal responsive elements (MREs) that are present in the MT promoter. This promoter also contains several constitutive (non-inducible) elements that bind transcription factors which do not need to be activated and that are responsible for a basal level of gene expression. As a result of the presence of these constitutive elements, the non-induced level of expression of the MT promoter is significant and the induction ratio (the ratio between the inducible expression and the basal level of expression) is usually no greater than 5- to 10-fold. Attempts have been made to reduce the basal level of expression by removing some of the constitutive elements of the MT promoter. The removal of these elements, however, also reduces the inducible level of expression.

The native human MT-IIA promoter, besides having the MREs and the constitutive elements, contains a single inducible glucocorticoid responsive element (GRE) and glucocorticoids, such as dexamethasone (dex), induce low levels of expression from the MT-IIA promoter in its native context.

The native MMTV-LTR promoter contains four inducible GREs and can be strongly induced by glucocorticoids. The basal level of expression is lower than that obtained with the human MT-IIA promoter but the absolute level of inducible expression is not as high.

Nucleic acid sequences, such as inducible elements, involved in the regulation of gene expression, may be located 5' to, 3' to, or within the regulated gene.

SUMMARY OF INVENTION

In accordance with the present invention, there is provided a synthetic inducible eukaryotic promoter for the regulation of transcription of a gene, comprising at least two different classes of inducible elements. Classes of inducible elements with which the invention is concerned include hormone-responsive elements (including GREs), metal-responsive elements (MREs), heat shock-responsive elements, interferon-responsive elements and cytokine responsive elements.

In one embodiment, the synthetic promoter provided herein is derived from a native promoter and one of the different classes of inducible elements is a native inducible element while another of the different classes of inducible elements is provided, such as by insertion into the native promoter or by activation of a normally-inactive element in the native promoter. While, in general two different classes of inducible elements are present in the novel synthetic promoter of the invention, combinations of three or more may be present, if desired.

The utilization of different classes of inducible elements in the synthetic promoters enables synergistic induction of a expression of a gene product in a eukaryotic expression system, particularly a mammalian expression system. That is, the level of gene expression obtained by induction of multiple classes of inducible element is greater than the sum of the individual gene expressions achieved by separate induction of the individual classes of inducible elements. In addition, overall levels of gene expression may be enhanced.

The synthetic promoters provided herein generally are derived from natural promoters by modification, as described in more detail herein, although such promoters also may be produced synthetically.

As mentioned above, inducible promoters may contain at least one constitutive element, which provides a basal level of gene expression in the absence of induction. In one embodiment of the invention, at least one constitutive element is functionally disabled, which generally results in a decreased level of basal gene, expression and an increased ratio of induced gene expression to basal gene expression, when compared to the unmodified promoter. Such functional disablement of the at least one constitutive element may be effected by deletion from the native promoter and/or by insertion, for example, of an inducible element therein.

The present invention, therefore, provides, in preferred embodiments, improved inducible eukaryotic promoters containing not only native GREs and/or MREs but also additional GREs and/or MREs. Constitutive elements of native promoters may or may not be deleted in the improved promoters. The improved promoters may be synergistically induced when both a heavy metal ion and a glucocorticoid (such as dexamethasone) are used at the same time and both at least one MRE and at least one GRE are present. Synergistic induction results in levels of gene expression that are much higher than those observed with unmodified promoters, such as the human MT-IIA or MMTV-LTR promoters. The new promoters also may contain fewer constitutive elements than unmodified promoters, which allows for a lower basal level of gene expression.

Conveniently the unmodified promoter may be the human MT-IIA or MMTV-LTR promoter. The responsive elements may conveniently contain the consensus sequence for such elements, for example, 5'-GATCTTGCGCCCGGCCCG-3' (SEQ ID NO: 2) contains-the MRE consensus sequence, and 5'-GATCTGGTACAGGATGTTCTAGCTACG-3' (SEQ ID NO: 1) contains the GRE. consensus sequence used in the embodiments of this invention.

Advantages of the present invention include:
  a) high overall levels of gene expression,
  b) decreased levels of basal gene expression,
  c) synergistic induction of expression of a gene,
  d) promoters-customized with regard to induction ratio and/or responsiveness to convenient inducers.

GENERAL DESCRIPTION OF INVENTION

Figure 1:
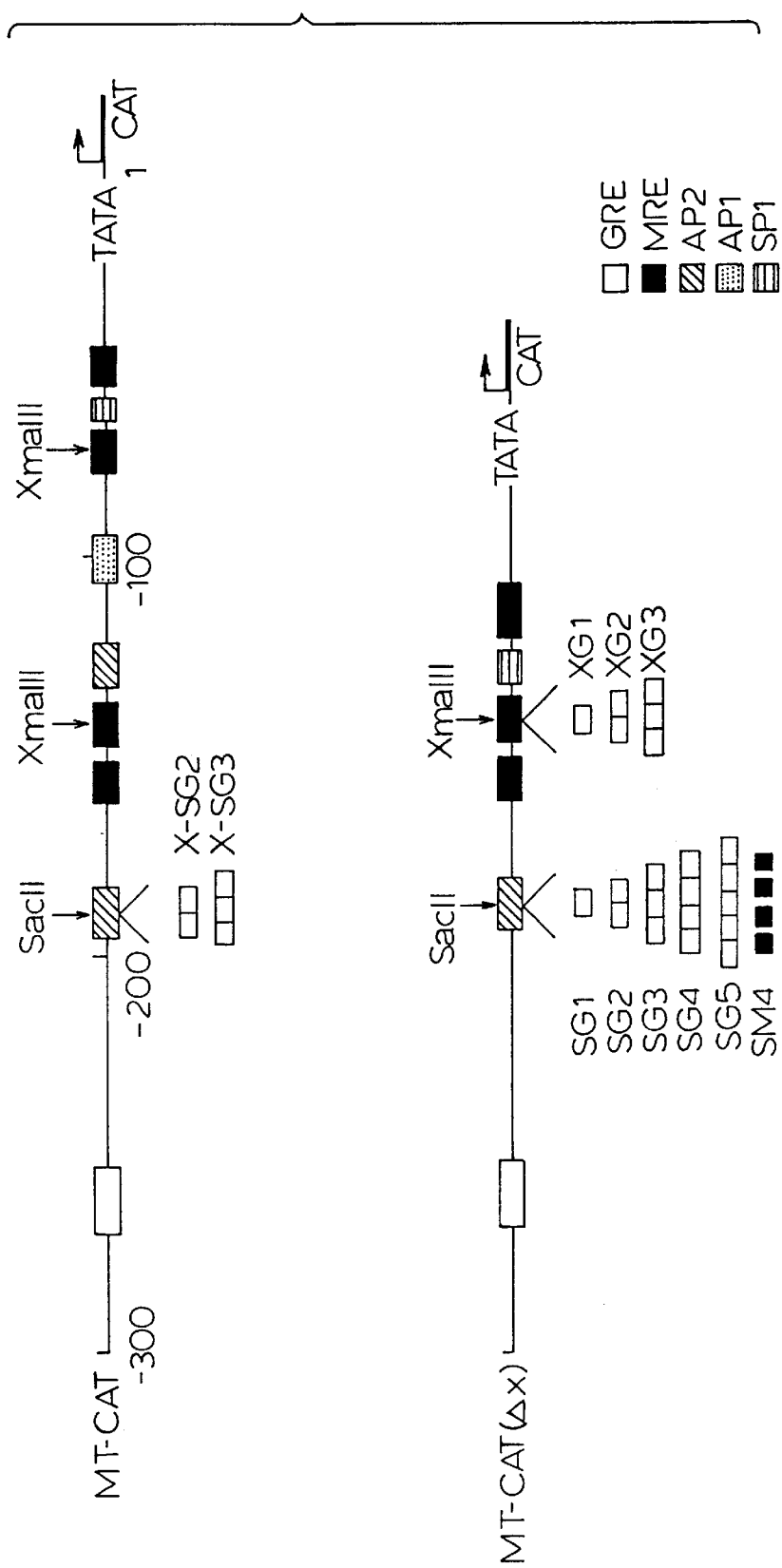
FIG. 1 is a genetic map of the hMT-IIA promoter and of a modified promoter with various modifications effected to the hMT-IIA promoter in accordance with one embodiment of the present invention.

As noted above, the novel promoter provided herein may be derived from a native promoter. In one preferred embodiment of the invention, the promoter contains at least one native inducible element which is an MRE and at least one different inducible element which is a hormone responsive element, particularly a glucocorticoid responsive element (GRE) provided in the native promoter by insertion.

Such an inserted GRE may be a synthetic molecule comprising a pair of complementary oligonucleotides containing the GRE consensus sequence. A plurality of GREs may be inserted into the native promoter in the form of a multimeric head-to-tail self-ligated element.

A particularly preferred embodiment of the invention provides a human metallothionein gene (hMT-IIA) promoter modified to contain at least one inducible GRE, so as to obtain a synergy of gene expression upon induction of the inducible MREs and GREs in a eukaryotic expression system, particularly a mammalian expression system, and preferably combined with an enhanced overall level of gene product expression. In this particularly preferred embodiment, multimeric head-to-tail GREs may be inserted into the native hMT-IIA promoter.

It is preferred also to disable at least one constitutive element of the native hMT-IIA promoter, such as by deletion of such element and/or by insertion of at least one GRE therein. In one illustrative Example, both deletion of constitutive elements and insertion of single or multiple GREs are employed to disable constitutive elements.

In another preferred embodiment of the invention, the promoter contains at least one native inducible element which is an HRE, particularly a glucocorticoid responsive element (GRE), and at least one different inducible element which is a MRE provided by insertion.

Such inserted MRE may be a synthetic molecule comprising a pair of complementary oligonucleotides containing the MRE consensus sequence. A plurality of MREs may be inserted into the native promoter in the form of a multimeric head-to-tail self-ligated element.

A particularly preferred embodiment of the invention provides a mouse mammary tumor virus/long terminal repeat (MMTV-LTR) promoter, modified to contain at least one inducible MRE, so as to obtain a synergy of gene expression upon induction of the inducible GREs and MREs in a eukaryotic expression system,. and preferably combined with an enhanced overall level of gene expression. In this particularly preferred embodiment, multimeric head-to-tail MREs may be inserted into the native MMTV-LTR promoter.

The novel synthetic inducible eukaryotic promoter provided herein may be incorporated into a vector for eukaryotic expression of a gene product, particularly when operatively connected to a gene to be expressed by the expression system. Such expression system may comprise eukaryotic cells containing the vector, particularly mammalian cells, such as Vero, CHO, HeLa, RatII fibroblasts and intestinal epithelial cells.

DESCRIPTION OF PREFERRED EMBODIMENT

In FIG. 1, there are shown different versions of a new promoter incorporating various modifications in accordance with embodiments of the present invention. The new series of promoters are generated using the following methodology. A KspI DNA fragment containing 800 bp of the 5' promoter region of the human MT-IIA gene (bases −740 to +60) was isolated from a plasmid containing the human MT-IIA gene (see Karin et al, (1982) Nature, 299, 797–802). After generating blunt ends, HindIII linkers were added and the fragment was inserted into pSVOATCAT, a plasmid containing the chloramphenicol acetyl transferase (CAT) gene used as a reporter gene, at the HindIII site 5' to the CAT gene. Two constitutive elements (AP1 and AP2 —see upper map, FIG. 1) of the original MT-IIA promoter were deleted by removing an XmaIII fragment (bases −79 to −129).

A pair of complementary oligonucleotides containing the GRE consensus sequence, a 5' BamHI site and a 3' BglII site was synthesized. The positive strand oligonucleotide sequence was:

5'-GATCTGGTACAGGATGTTCTAGCTACG-3' (SEQ ID NO: 1) Multimeric head-to-tail GREs were prepared by self-ligating the synthetic GRE oligonucleotide in the presence of BamHI and BglII. Single and multimeric GREs were inserted into the SacII site of the promoter (at base −175) or the XmaIII site of the promoter (at base −129) (see lower map in FIG. 1). The insertion at the SacII element destroys a second AP2 site.

A pair of complementary oligonucleotides containing the MRE consensus sequence, a 5' BamHI site and a 3' BglII site was synthesized. The positive strand nucleotide sequence was:

5'-GATCTTGCGCCCGGCCCG-3' (SEQ ID NO: 2) Such oligonucleotides may be used to synthesize multimeric head-to-tail elements and single or multiple MREs may be inserted into the hMT-IIA promoter in an analogous manner to the GREs.

The MMTV-CAT vector for effecting similar GRE and/or MRE insertions to and optionally constitutive element deletions from the MMTV-LTR promoter was removed from plasmid p201 (Majors et al, (1981), Nature, 283, 253–258) using PstI and, after generation of blunt ends, inserted into the HindIII site of pSVOATCAT.

The new promoters were tested in transient CAT expression assays using RAT II fibroblasts, CHO (chinese hamster ovarian cells), VERO (monkey fibroblasts) and Hela (human cervical tumour cells) cells, expressing the glucocorticoid receptor. The results, reproduced in the Examples below, indicated that these new promoters generate very high levels of expression when cells normally expressing the glucocorticoid receptor or transfected with the glucocorticoid receptor gene are simultaneously induced with heavy metal ions and dexamethasone. The induced levels of expression obtained with these promoters are significantly higher than those observed with the wild-type human MT-IIA or MMTV-LTR promoters. At the same time the basal level of expression was significantly lower than that observed with the wild-type human MT-IIA promoter.

EXAMPLES

The above disclosure generally describes the present invention. A more complete understanding can be obtained by reference to the following specific examples. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

EXAMPLE 1

This Example illustrates the construction of modified hMT-IIA promoters containing additional GREs.

All MT expression vectors were derived from pSVOATCAT, a plasmid containing the chloramphenicol acetyl transferase (CAT) gene without any regulatory sequences (Gorman et al., Mol.Cell.Biol., 2, 1044, [1982]). MT-CAT, a control plasmid in which the CAT gene is under the regulation of the wild-type human MT-IIA promoter (hMT-IIA), was generated as described below. An 800 bp KspI fragment of the promoter region of the hMT-IIA (bases −740 to +60) (FIG. 1) was isolated. After generating blunt ends, HindIII linkers were added and the fragment was inserted into the HindIII site of pSVOATCAT, 5' to the CAT gene. Plasmid MT-CAT-ΔX was generated by removing the XmaIII fragment (base −79 to −129) from the MT promoter of MT-CAT which contains the constitutive AP1–AP2 elements. To insert additional GREs, a pair of complementary oligonucleotides containing the GRE consensus sequence, a 5' BamHI site and a 3' BglII site were synthesized and multimeric head-to-tail elements were generated by self-ligating these synthetic sequences in the presence of BamHI and BglII. The positive strand nucleotide sequence was SEQ ID NO: 1, as specified above. Monomeric or multimeric GREs then were inserted at either the SacII or the XmaIII site of the MT-CAT-66 X vector after generation of blunt ends (FIG. 1). The number of GREs inserted was confirmed by DNA sequencing.

EXAMPLE 2

This Example illustrates the use of an expression vector containing additional GREs.

The expression vector used in this example was SG2, which is a pSVOATCAT-derived CAT expression vector containing a modified MT-IIA promoter in which two additional GREs were inserted at the SacII site of MT-CAT-ΔX (FIG. 1). Fifteen μg of plasmid DNA were transfected into CHO cells using the calcium phosphate procedure (Graham et al (1973) Virology, 52, 456–467). After incubation for 5 hours at 37° C., the cells were shocked for 3 minutes with 15% glycerol in PBS. The monolayers then were incubated with the different inducers ($CdCl_2$ and/or dexamethasone) for 16 hours and cell extracts were prepared. The CAT activity then was measured using $^{14}$C-Chloramphenicol as substrate and the radioactive acetylated product was extracted with xylene. Radioactive counts were determined in a scintillation counter.

In addition, the SG2 vector was compared with two other vectors that were constructed by inserting a wild-type MT-IIA promoter and the MMTV-LTR promoter into the HindIII site of the pSVOATCAT plasmid. Since CHO cells do not have glucocorticoid receptors, the cells were co-transfected with 10 μg of a glucocorticoid receptor expression vector (Giguere et al, (1986) Cell, 46, 645–652). CAT expression assays were performed in quadruplicate and the standard deviation did not exceed 10%. Protein concentration was measured in each cell lysate and CAT activity was calculated for equivalent amounts of protein. The results from these experiments are summarised in Table I below. (The Tables appear at the end of the descriptive text).

The results appearing in Table I show that the synergistic induction of the SG2 promoter with metals and dexamethasone generated a higher level of CAT gene expression than the wild-type MT-IIA and the MMTV-LTR promoters. At the same time, the induction ratio also was significantly improved.

EXAMPLE 3

This Example further illustrates the use of a vector containing additional GREs.

Using a procedure similar to that of Example 1, the activity of the SG2 promoter was compared with that of the native MT-IIA promoter in VERO cells engineered to express glucocorticoid receptors (Giguere et al, (1986) Cell, 46, 645–652). In this Example, the cells also were co-transfected with an expression vector in which the β-galactosidase gene was driven by a promoter, whose activity was not affected under the experimental conditions by heavy metals or glucocorticoids. After transfection and induction, an aliquot of the cell extract was used to measure the β-galactosidase (β-Gal) activity. This activity was used to standardize CAT activity measurements by taking into account the efficiency of transfection.

The results obtained are shown in Table II below, and it can be seen that they are very similar to those obtained with CHO cells (Table I) and demonstrate that dexamethasone acts synergistically with metal ions on the modified MT-IIA (SG2) promoter.

EXAMPLE 4

This Example illustrates further modification to the expression vector and the results obtained.

Additional modifications were effected to the hMT-IIA promoter to introduce additional numbers of GREs and multiple MREs at the SacII site and to introduce numbers of GREs at the XmaIII site, as detailed in FIG. 1.

The resulting modified plasmid DNA was introduced into Vero cells as described in Example 3 and CAT gene expression was determined as described above. The results obtained are set forth in Table III below.

EXAMPLE 5

This Example illustrates the construction and use of a modified MMTV-LTR promoter containing additional GREs.

Two MREs were inserted, using a similar procedure to previous examples, at the BfrI site of the MMTV-LTR promoter, which contains four GREs but has no MREs (Majors and Varmus, Nature 283: 253–258). Table IV shows that while the unmodified MMTV-LTR promoter was not inducible by Zn plus Cd, the modified promoter (BM2-MMTV) displayed a ten-fold induction. When BM2-MMTV was induced by dexamethasone plus Zn plus Cd a two-fold synergy in CAT expression was observed.

The results of the experiments represented in Examples 1 to 5 and Tables I to IV show that it is possible to achieve synergistic activation of transcription in the context of a modified hMT-IIA promoter by inserting additional inducible elements in the form of GREs and in the context of a modified MMTV promoter by inserting additional inducible elements in the form of MREs. Addition of the GREs to the hMT-IIA promoter and MREs to the MMTV promoter did not increase the basal level of reporter gene expression and the inducibility and transcriptional strength of the modified promoters were significantly improved over those of their wild-type counterpart. In contrast the exclusive insertion of four extra MREs (vector SM4) to the hMT-IIA promoter resulted only in a moderate improvement in MT promoter transcriptional strength and this improvement was accompanied by a significant increase in basal expression.

The unmodified hMT-IIA promoter in the MT-CAT vector could not be induced by dexamethasone in Vero cells transfected with the glucocorticoid receptor gene. However, the insertion of at least one additional GRE to the promoter was enough to confer glucocorticoid responsiveness and gene expression.

To analyze the impact of the number of additional GREs inserted and the site of insertion, two series of modified promoters were generated in the Examples by adding one or more GREs at either SacII site (SG series) or the XmaIII site (XG series) of MT-CAT-66 X. All vectors were inducible by $CdCl_2$ and glucocorticoids. However, a minimum of two adjacent GREs was necessary to generate synergistic inducibility by simultaneous treatment of transfected Vero cells with $CdCl_2$ and dexamethasone, regardless of the site of insertion.

The induction ratio calculated for the modified hMT-IIA promoters was increased up to 6-fold as compared to the wild-type promoter. The fact that the insertion of additional GREs did not increase the basal level of gene expression in, for example, SG3 is an important factor in the improvement of this ratio. This observation emphasizes one of the advantages of generating synergistic transcription activation by adding different classes of inducible elements rather than constitutive ones, in accordance with the present invention.

SUMMARY OF DISCLOSURE

In summary of this disclosure, the inventors provide for the engineering and use of novel and improved inducible mammalian expression systems, in particular, the preparation and use of modified human MT-IIA promoters containing one or several additional glucocorticoid-responsive elements which can be synergistically induced by glucocorticoids and metal ions while maintaining a low level of basal gene expression. The induction ratio may be increased further by deleting constitutive elements. A similar strategy may be used to generate improved mouse mammary tumour virus (MMTV) promoter by inserting additional metal-responsive elements. Modifications are possible within the scope of this invention.

TABLE I

| Promoter | Inducer | CAT Activity (cpm) |
|---|---|---|
| MT-IIA | Control | 5932 |
| MT-IIA | 100 μM $ZnCl_2$ + 2 μM $CdCl_2$ | 70235 |
| MT-IIA | 1 μM Dexamethasone | 3935 |
| MT-IIA | 100 μM $ZnCl_2$ + 1 μM Dexamethasone | 70119 (12x)* |
| SG 2 | Control | 2893 |
| SG 2 | 100 μM $ZnCl_2$ + 2 μM $CCl_3$ | 22901 |
| SG 2 | 1 μM Dexamethasone | 97068 |
| SG 2 | 100 μM $ZnCl_2$ + 2 μM $CdCl_2$ + 1 μM Dexamethasone | 147713 (57x)* |
| MMTV-LTR | Control | 751 |
| MMTV-LTR | 1 μM Dexamethasone | 20310 (27x)* |

*Induction Ratio

TABLE II

| Promoter | Inducer | Standardised CAT Activity (U CAT/β-GAL) |
|---|---|---|
| MT-IIA | Control | 19 |
| MT-IIA | 5 μM $CdCl_2$ | 574 |
| MT-IIA | 1 μM Dexamethasone | 40 |
| MT-IIA | 5 μM $CdCl_2$ + μM Dexamethasone | 526 (27x)* |
| SG 2 | Control | 8 |
| SG 2 | 5 μM $CdCl_2$ | 114 |
| SG 2 | 1 μM Dexamethasone | 230 |
| SG 2 | 5 μM $CdCl_2$ + 1 μM Dexamethasone | 1072 (134x)* |

*Induction Ratio

TABLE III

| Promoter | Inducer | Relative CAT activity (% of MT-IIA control) |
|---|---|---|
| MT-IIA | Control | 100 |
| MT-IIA | 5 uM $CdCl_2$ | 1064 |
| MT-IIA | 1 uM Dexamethasone | 103 |
| MT-IIA | 5 uM $CdCl_2$ + 1 uM Dexamethasone | 1074 |
| SG1 | Control | 32 |
| SG1 | 5 uM $CdCl_2$ | 328 |
| SG1 | 1 uM Dexamethasone | 957 |
| SG1 | 5 uM $CdCl_2$ + 1 uM Dexamethasone | 1364 |
| SG2 | Control | 36 |
| SG2 | 5 uM $CdCl_2$ | 364 |
| SG2 | 1 uM Dexamethsone | 1164 |
| SG2 | 5 uM $CdCl_2$ + 1 uM Dexamethasone | 2324 |
| SG3 | Control | 50 |
| SG3 | 5 uM $CdCl_2$ | 596 |
| SG3 | 1 uM Dexamethasone | 1821 |
| SG3 | 5 uM $CdCl_2$ + 1 uM Dexamethasone | 3156 |
| SG4 | Control | 29 |
| SG4 | 5 uM $CdCl_2$ | 210 |
| SG4 | 1 uM Dexamethasone | 386 |
| SG4 | 5 uM $CdCl_2$ + 1 uM Dexamethasone | 1317 |
| SG5 | Control | 21 |
| SG5 | 5 uM $CdCl_2$ | 200 |
| SG5 | 1 uM Dexamethasone | 136 |
| SG5 | 5 uM $CdCl_2$ + 1 uM Dexamethasone | 1117 |
| XG1 | Control | 46 |
| XG1 | 5 uM $CdCl_2$ | 1755 |
| XG1 | 1 uM Dexamethasone | 275 |
| XG1 | 5 uM $CdCl_2$ + 1 uM Dexamethasone | 1574 |
| XG2 | Control | 12 |
| XG2 | 5 uM $CdCl_2$ | 519 |
| XG2 | 1 uM Dexamethasone | 394 |
| XG2 | 5 uM $CdCl_2$ + 1 uM Dexamethasone | 1957 |
| XG3 | Control | 11 |
| XG3 | 5 uM $CdCl_2$ | 107 |
| XG3 | 1 uM Dexamethasone | 36 |
| XG3 | 5 uM $CdCl_2$ + 1 uM Dexamethasone | 229 |
| X-SG2 | Control | 84 |
| X-SG2 | 5 uM $CdCl_2$ | 1482 |
| X-SG2 | 1 uM Dexamethasone | 495 |
| X-SG2 | 5 uM $CdCl_2$ + 1 uM Dexamethasone | 2562 |
| X-SG3 | Control | 146 |
| X-SG3 | 5 uM $CdCl_2$ | 1145 |
| X-SG3 | 1 uM Dexamethasone | 833 |
| X-SG3 | 5 uM $CdCl_2$ + 1 uM Dexamethasone | 3383 |
| SM4 | Control | 393 |

TABLE III-continued

| Promoter | Inducer | Relative CAT activity (% of MT-IIA control) |
|---|---|---|
| SM4 | 5 uM CdCl$_2$ | 1485 |
| SM4 | 1 uM Dexamethasone | 382 |
| SM4 | 5 uM CdCl$_2$ + 1 uM Dexamethasone | 1524 |

TABLE IV

| Promoter | Inducer | Standardised CAT activity (CPM) |
|---|---|---|
| MMTV-LTR | control | 1326 |
| MMTV-LTR | Dex | 135405 |
| MMTV-LTR | Zn + Cd | 225 |
| MMTV-LTR | Zn + Cd + Dex | 145416 (102X)* |
| BM2-MMTV | control | 1078 |
| BM2-MMTV | Dex | 92899 |
| BM2-MMTV | Zn + Cd | 10827 |
| BM2-MMTV | Zn + Cd + Dex | 196614 (182X)* |

*Induction ratio.

expression by said promoter and to increase the ratio of induced to basal gene expression by said promoter.

2. The promoter of claim 1 wherein said at least one constitutive element is disabled by deletion from the native promoter or insertion of an inducible element into the native promoter.

3. A synthetic inducible eukaryotic promoter for the regulation of transcription of a gene, comprising at least two different classes of inducible elements, wherein said different classes of inducible elements are selected to provide a synergistic level of expression of a gene product in a eukaryotic expression system, said promoter being derived from a native promoter and one of said different classes of inducible elements is a native inducible element and another of said different classes of inducible elements is a different inducible element provided in said native promoter, wherein said native inducible element is a metal-responsive element (MRE) and said different inducible element is at least one glucocorticoid-responsive element (GRE) and is provided in said native promoter by insertion.

4. The promoter of claim 3 wherein said inserted GRE is a synthetic molecule containing the GRE consensus sequence and having a positive strand having the nucleotide sequence:

What we claim is:

1. A synthetic inducible eukaryotic promoter for the regulation of transcription of a gene, comprising at least two different classes of inducible elements, wherein said different classes of inducible elements are selected to provide a synergistic level of expression of a gene product in a eukaryotic expression system, said promoter being derived from a native promoter containing at least one constitutive element, wherein said at least one constitutive element is functionally disabled to decrease the level of basal gene

5'-GATCTGGTACAGGATGTTCTAGCTACG-3' (SEQ ID NO: 1).

5. The promoter of claim 4 wherein a plurality of GREs is inserted in said native promoter in the form of a multimeric head-to-tail element self-ligated in the presence of BamHI and BglII.

6. The promoter of claim 3 which is derived from a native promoter containing at least one constitutive element and wherein said at least one constitutive element is functionally disabled.

7. The promoter of claim 6 wherein said at least one constitutive element is disabled by deletion of the constitutive element from the native promoter or insertion of an inducible element in the constitutive element.

8. The promoter of claim 7 wherein said at least one constitutive element is functionally disabled sufficient to provide a decreased level of basal gene expression and an increased ratio of induced gene expression.

9. The promoter of claim 8 wherein said native promoter is the hMT-IIA promoter.

10. The promoter of claim 3 wherein said native promoter is the hMT-IIA promoter.

11. The promoter of claim 8 wherein said at least one GRE is inserted at either the SacII site at base −175 or the XmaIII site at base −129 or at both the SacII and the XmaIII sites of a native hMT-IIA promoter.

12. A synthetic inducible eukaryotic promoter for the regulation of transcription of a gene, comprising at least two different classes of inducible elements, wherein said different classes of inducible elements are selected to provide a synergistic level of expression of a gene product in a eukaryotic expression system, said promoter being derived from a native promoter and one of said different classes of inducible elements is a native inducible element and another of said different classes of inducible elements is a different inducible element provided in said native promoter, wherein said native inducible element is a metal responsive element (MRE) and said different inducible element is a glucocorticoid-responsive element (GRE) and is provided in said native promoter by insertion, wherein said native promoter is the hMT-IIA promoter, wherein multiple linked GRE's are inserted into the native promoter.

13. The promoter of claim 10 wherein at least one native constitutive element is disabled.

14. The promoter of claim 13 wherein said constitutive element is disabled by deletion and/or insertion of at least one GRE therein.

15. The promoter of claim 14 wherein two native constitutive elements, AP1 and AP2, located between bases −79 to −129 of the native hMT-IIA promoter are deleted.

16. The promoter of claim 15 wherein at least one GRE sequence is inserted at the SacII site (base −175) of the native hMT-IIA promoter thereby disabling a second AP2 constitutive element at that location.

17. The promoter of claim 12 wherein two linked GRE sequences are inserted at the XmaIII site at base −129 of the hMT-IIA promoter.

18. The promoter of claim 12 wherein three linked GRE sequences are inserted at the SacII site at base −175 of the hMT-IIA promoter.

19. A synthetic inducible eukaryotic promoter for the regulation of transcription of a gene, comprising at least two different classes of inducible elements, wherein said different classes of inducible elements are selected to provide a synergistic level of expression of a gene product in a eukaryotic expression system, said promoter being derived from a native promoter and one of said different classes of inducible elements is a native inducible element and another of said different classes of inducible elements is a different inducible element provided in said native promoter, wherein said native responsive element is a glucocorticoid-responsive element (GRE) and said different inducible element is a metal responsive element (MRE) which is provided in said native promoter by insertion.

20. The promoter of claim 19 wherein said inserted MRE is a synthetic molecule containing the MRE consensus sequence and having a-positive strand having the nucleotide sequence:

5'-GATCTTGCGCCCGGCCCG-3' (SEQ ID NO: 2).

21. The promoter of claim 20 wherein a plurality of MREs is inserted into the native promoter in the form of a multimeric head-to-tail element self-ligated in the presence of BamHI and BglII.

22. The promoter of claim 19 wherein said native promoter is the MMTV-LTR promoter.

23. A synthetic inducible eukaryotic promoter for the regulation of transcription of a gene, comprising at least two different classes of inducible elements, wherein said different classes of inducible elements are selected to provide a synergistic level of expression of a gene product in a eukaryotic expression system, said promoter being derived from a native promoter and one of said different classes of inducible elements is a element is a native inducible element and another of said different classes of inducible elements is a different inducible element provided in said native promoter, wherein said native responsive element is a glucocorticoid-responsive element (GRE) and said different inducible element is a metal responsive element (MRE) which is provided in said native promoter by insertion, wherein said native promoter is the MMTV-LTR promoter, wherein at least two linked MRE's are inserted into the native promoter.

24. A vector for eukaryotic expression of a gene product, comprising a synthetic inducible eukaryotic promoter operatively connected to a gene encoding said gene product said promoter being a modified native hMT-IIA promoter as claimed in claim 10.

25. A vector for eukaryotic expression of a gene product, comprising a synthetic inducible eukaryotic promoter operatively connected to a gene encoding said gene product, said promoter being a modified native MMTV-LTR promoter as claimed in claim 22.

26. A eukaryotic expression system, comprising eukaryotic cells containing a vector as claimed in claim 24 or 25 for effecting induced gene expression.

27. The expression system of claim 26 wherein said eukaryotic cells are mammalian cells.

28. The expression system of claim 27 wherein said mammalian cells are selected from Vero, CHO, HeLa, RatII and epithelial cells.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 1:

GATCTGGTAC AGGATGTTCT AGCTACG                                                                                                                                                              27

( 2 ) INFORMATION FOR SEQ ID NO: 2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 2:

GATCTTGCGC CCGGCCCG                                                                                                                                                                              18